United States Patent [19]

Lebkuecher et al.

[11] 4,376,771

[45] Mar. 15, 1983

[54] 6-(P-ACYLAMINOPHENYL)-4,5-DIHYDROPYRIDAZ-3-ONES AND THERAPEUTIC AGENTS CONTAINING SAID COMPOUNDS

[75] Inventors: Rolf Lebkuecher; Marco Thyes; Horst Koenig, all of Ludwigshafen; Hans D. Lehmann, Hirschberg-Leutershausen; Josef Gries, Wachenheim; Dieter Lenke, Ludwigshafen; Johannes Kunze, Plattling, all of Fed. Rep. of Germany

[73] Assignee: BASF Aktiengesellschaft, Fed. Rep. of Germany

[21] Appl. No.: 224,939

[22] Filed: Jan. 14, 1981

Related U.S. Application Data

[63] Continuation of Ser. No. 101,537, Dec. 10, 1979, abandoned, which is a continuation of Ser. No. 913,642, Jun. 8, 1978, abandoned.

[30] Foreign Application Priority Data

Jun. 18, 1977 [DE] Fed. Rep. of Germany ....... 2727481

[51] Int. Cl.³ .................... C07D 237/04; A61K 31/50
[52] U.S. Cl. ...................................... 424/250; 544/239
[58] Field of Search ......................... 544/239; 424/250

[56] References Cited

U.S. PATENT DOCUMENTS

| | | | |
|---|---|---|---|
| 3,475,431 | 10/1969 | Bachmann | 424/250 |
| 3,689,652 | 9/1972 | Curran et al. | 424/250 |
| 3,746,712 | 6/1973 | Ross | 424/250 |
| 3,806,509 | 10/1969 | Lebkuecher et al. | 424/250 |
| 3,812,256 | 5/1974 | Curran | 424/250 |
| 3,822,260 | 7/1974 | Curran et al. | 424/250 |
| 3,824,271 | 6/1974 | Allen, Jr. | 424/250 |
| 3,845,050 | 10/1974 | Lebkuecher et al. | 424/250 |
| 3,975,388 | 8/1976 | Hakim | 424/250 |
| 4,112,095 | 9/1978 | Allen, Jr. | 424/250 |

*Primary Examiner*—Mark L. Berch
*Attorney, Agent, or Firm*—Keil & Witherspoon

[57] ABSTRACT

6-(p-Acylaminophenyl)-4,5-dihydropyridaz-3-ones of the formula I

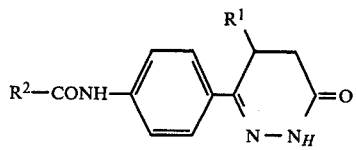

where $R^1$ is hydrogen or alkyl of 1 to 3 carbon atoms and $R^2$, if $R^1$ is hydrogen, is halogen-substituted alkyl of 3 to 6 carbon atoms or β-haloethyl or, if $R^1$ is alkyl of 1 to 3 carbon atoms, is halogen-substituted alkyl of 1 to 6 carbon atoms, their manufacture, and therapeutic agents which contain, as the active ingredient, a compound of the formula I, where $R^2$ may also be halomethyl or α-haloethyl if $R^1$ is hydrogen. These compounds may be used as anti-hypertensive agents and for the prophylaxis and therapy of thromboembolic disorders.

6 Claims, No Drawings

6-(P-ACYLAMINOPHENYL)-4,5-DIHYDROPYRIDAZ-3-ONES AND THERAPEUTIC AGENTS CONTAINING SAID COMPOUNDS

This is a continuation of application Ser. No. 101,537, filed Dec. 10, 1979, abandoned which is a continuation of Ser. No. 913,642, filed June 8, 1978 abandoned.

The present invention relates to 6-(p-acylaminophenyl)-4,5-dihydropyridaz-3-ones, their manufacture and pharmaceutical formulations which contain 6-(p-acylaminophenyl)-4,5-dihydropyridaz-3-ones.

We have found that 6-(p-acylaminophenyl)-4,5-dihydropyridaz-3-ones, in which acyl is halogen-substituted, of the formula I

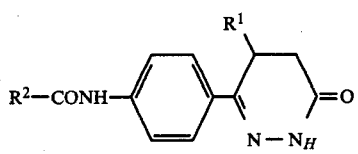

where $R^1$ is hydrogen or alkyl of 1 to 3 carbon atoms and $R^2$, if $R^1$ is hydrogen, is halogen-substituted alkyl of 3 to 6 carbon atoms or β-haloethyl or, if $R^1$ is alkyl of 1 to 3 carbon atoms, is halogen-substituted alkyl of 1 to 6 carbon atoms, having valuable pharmacological properties.

Alkyl $R^1$ is in particular methyl, ethyl or propyl.

Halogen-substituted alkyl $R^2$, if $R^1$ is hydrogen, is, for example, 2-chloroethyl, 2-bromoethyl, 2-fluoroethyl, 2-iodoethyl, 1-chloropropyl, 1-bromopropyl, 1-fluoropropyl, 1-iodopropyl, 2-chloropropyl, 3-chloropropyl, 3-bromopropyl, 3-fluoropropyl, 3-iodopropyl, 1-chloroisopropyl, 1-bromoisopropyl, 1-iodoisopropyl, 2-chloroisopropyl, 2-bromoisopropyl, 1-chlorobutyl, 1-bromobutyl, 1-fluorobutyl, 4-chlorobutyl, 4-bromobutyl, 4-fluorobutyl, 1-chloroisobutyl, 1-bromoisobutyl, 2-chloroisobutyl, 1-chloro-sec.-butyl, 1-bromo-sec.-butyl, 3-chloro-sec.-butyl, chloro-tertiary butyl, bromo-tertiary butyl, 1-chloroamyl, 1-bromoamyl, 5-bromoamyl, 1-ethyl-1-chloropropyl and 1-ethyl-1-bromopropyl.

Where $R^1$ is alkyl, $R^2$ may, in addition to having the above meanings, also be, for example, chloromethyl, bromomethyl, fluoromethyl, iodomethyl, 1-chloroethyl, 1-bromoethyl, 1-fluoroethyl or 1-iodoethyl.

Preferred compounds are those in which $R^1$ is hydrogen or methyl and $R^2$, if $R^1$ is hydrogen, is halogen-substituted, especially chlorine-substituted or bromine-substituted, alkyl of 3 or 4 carbon atoms or is β-haloethyl or, if $R^1$ is methyl, halogen-substituted, especially chlorine-substituted or bromine-substituted, alkyl of 1 to 4 carbon atoms.

The compounds of the formula I may be manufactured by reacting a compound of the formula II

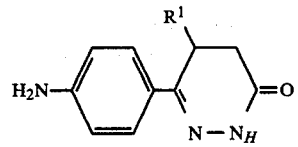

where $R^1$ has the above meanings, in the conventional manner with an acylating agent of the formula III $$R^2COY \qquad III$$

where Y is OH, chlorine, bromine, lower alkoxy or $OCOR^2$.

In accordance with the meanings given for Y, advantageous acylating agents are the corresponding carboxylic acids, carboxylic acid halides, especially chlorides and bromides, carboxylic acid esters, especially methyl esters and ethyl esters, and carboxylic acid anhydrides.

The acylation is carried out under conventional conditions, as a rule with at least an equimolar amount of the acylating agent, advantageously in the presence of a solvent and in the presence or absence of an auxiliary base, at from 0° C. to 160° C., if appropriate at the boiling point of the reaction mixture, and under atmospheric or superatmospheric pressure.

Suitable solvents are those which are inert under the reaction conditions, such as aromatic hydrocarbons, eg. benzene or toluene, cyclic aliphatic ethers, eg. dioxane, or dialkylformamides, eg. dimethylformamide. Advantageous auxiliary bases to use as acidbinding agents are inorganic bases, eg. sodium carbonate or potassium carbonate, sodium bicarbonate or potassium bicarbonate, or tertiary organic amines, eg. triethylamine.

The following equation illustrates the manufacture of the 6-(p-acylaminophenyl)-4,5-dihydropyridaz-3-ones of the formula I:

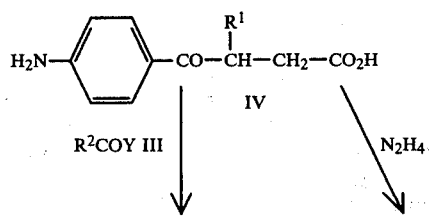

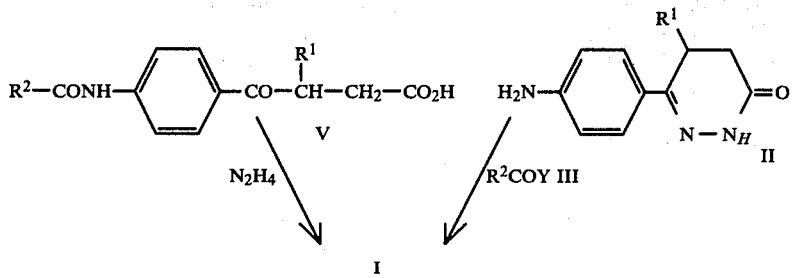

As shown above, the compounds of the formula I may be manufactured, according to a further embodiment, by acylating a compound of the formula IV, where $R^1$ has the above meanings, with an acylating agent of the formula III $$R^2COY \qquad III$$

where $R^2$ and Y have the above meanings, under the same conditions, and cyclizing the resulting acyl compound V

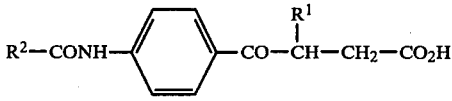

with hydrazine.

This cyclization reaction with hydrazine or hydrazine hydrate is advantageously carried out with an equimolecular amount of hydrazine in a solvent, especially a lower alcohol, eg. methanol, ethanol or propanol, a cyclic ether, eg. dioxane, or a dialkylformamide, eg. dimethylformamide, at from 60° to 150° C., preferably from 80° to 120° C.

The compounds of the formula II and of the formula IV which are used as starting materials are known or can be manufactured under the conditions described, for example, in German Laid-Open Applications DOS Nos. 1,670,158 and 2,150,436 or U.S. Pat. Nos. 3,824,271 and 3,888,901.

It is to be noted that the compounds where $R^1$ is not hydrogen contain an asymmetric carbon atom in the 5-position and exist in the form of racemates. The present invention also encompasses the enantiomers. If a separation is desired, it is advantageously carried out at the stage of the compound of the formula II, by conventional methods, using an optically active acid, eg. dibenzoyltartaric acid or camphor-10-sulfonic acid, via the formation of diastereomeric salts.

In addition to the compounds referred to in the Examples, the following may, for example, be obtained by the above processes: 6-(p-bromoacetylaminophenyl)-4,5-dihydropyridaz-3-one, 6-(p-bromoacetylaminophenyl)-5-methyl-4,5-dihydropyridaz-3-one, 6-(p-fluoroacetylaminophenyl)-5-methyl-4,5-dihydropyridaz-3-one, 6-(p-iodoacetylaminophenyl)-5-methyl-4,5-dihydropyridaz-3-one, 6-[p-(3-bromopropionylamino)-phenyl]-5-methyl-4,5-dihydropyridaz-3-one, 6-[p-(3-fluoropropionylamino)-phenyl]-5-methyl-4,5-dihydropyridaz-3-one, 6-[p-(3-iodopropionylamino)-phenyl]-5-methyl-4,5-dihydropyridaz-3-one, 6-[p-(2-chlorobutyrylamino)-phenyl]-4,5-dihydropyridaz-3-one, 6-[p-(2-chlorobutyrylamino)-phenyl]-5-methyl-4,5-dihydropyridaz-3-one, 6-[p-(3-chlorobutyrylamino)-phenyl-]5-methyl-4,5-dihydropyridaz-3-one, 6-[p-(2-bromovalerylamino)-phenyl]-5-methyl-4,5-dihydropyridaz-3-one, 6-[p-(2-bromoisovalerylamino)-phenyl]-5-methyl-4,5-dihydropyridaz-3-one and 6-[p-(2-ethyl-2-bromobutyrylamino)-phenyl]-5-methyl-4,5-dihydropyridaz-3-one.

Further, we have found that the new compounds of the formula I and also compounds of the formula I where, if $R^1$ is hydrogen, $R^2$ is halomethyl or α-haloethyl, are distinguished by a powerful thrombocyte aggregation-inhibiting action and an anti-hypertensive action. They may be used as anti-hypertensive agents and for the prophylaxis and therapy of thromboembolic disorders.

The following methods were used to examine the pharmacodynamic properties of the products of the invention:

1. Inhibition of the collagen-induced aggregation of human thrombocytes in vitro.

Thrombocyte-rich plasma is obtained by centrifuging venous citrate blood (300 g, 10 minutes duration at 4° C.). The photometric measurement of the thrombocyte aggregation is carried out with addition of $MgCl_2$ (final concentration 10 millimoles/l) and of collagen Stago (final concentration 0.02 mg/ml) in a Born Mk 3 aggregometer. The maximum extinction change/sec is used as a measure of the aggregation.

The aggregation-inhibiting activity of the substances is tested after an incubation time of 10 minutes.

The EC 50% is taken to be the concentration causing 50% inhibition of aggregation.

2. Inhibition of the collagen-induced aggregation of rat thrombocytes ex vivo.

The substances are administered orally to groups of 10–15 male Sprague-Dawley rats weighing 200–250 g. 2–4 hours after administration, blood is taken under ether narcosis and thrombocyte-rich plasma is obtained by centrifuging. The aggregation after addition of collagen is measured as indicated above.

The ED 33% is determined as the dose which inhibites the collagen-induced thrombocyte aggregation by 33%.

3. Anti-hypertensive effect on narcotized rats.

To test the anti-hypertensive effect, the substances are administered intraperitoneally to groups of 3–5 male Sprague-Dawley rats weighing 240–280 g, under urethane narcosis (1.78 mg/kg given intraperitoneally). The measurement of the blood pressure in the carotid artery is carried out by means of Statham transducers. The ED 20% is determined as the dose which lowers the mean carotid blood pressure by 20%.

4. Anti-hypertensive effect on spontaneously hypertonic rats.

The substances are administered orally to groups of 4-8 male spontaneously hypertonic Okamoto rats weighing 270-340 g.

Before, and 2 hours after, the administration, the systolic blood pressure is measured non-surgically by means of piezo-electric crystal sensors.

The ED 20% is determined as the dose which lowers the systolic pressure by 20%, taking into account the values found with untreated control animals.

The effective doses or effective concentrations were calculated from the linear relationships between the logarithm of the dose or concentration and the logarithm of the effect, by means of regression analysis.

Acetylsalicyclic acid was used as the reference substance for the inhibition of thrombocyte aggregation and dihydralazine was used as the reference substance for the anti-hypertensive effect.

TABLE 1

| Example No. | Inhibition of thrombocyte aggregation[2] | | Lowering of blood pressure[1] | |
|---|---|---|---|---|
| | EC 50% | R.E. | ED 20% | R.E. |
| 1 | 0.25 | 1,980 | 0.37 | 0.92 |
| 3 | 0.11 | 4,490 | 0.15 | 2.27 |
| 4 | 0.27 | 1,830 | 0.53 | 0.64 |
| 5 | 0.031 | 15,900 | 0.0079 | 43.04 |
| 6 | 0.35 | 1,410 | 10 | 0.03 |
| 7 | 0.30 | 1,650 | 0.045 | 7.56 |
| 8 | 1.70 | 291 | 0.32 | 1.06 |
| 9 | 0.27 | 1,830 | 1.49 | 0.23 |
| 11 | 0.47 | 1,050 | 0.61 | 0.56 |
| 12 | 0.44 | 1,120 | 0.34 | 1.00 |
| 16 | 0.58 | 852 | 0.40 | 0.85 |
| 17 | 0.89 | 555 | 2.93 | 0.12 |
| Dihydralazine | 149 | 3.32 | 0.34 | 1.00 |
| Acetylsalicylic acid | 494 | 1.00 | — | — |

[1]Rats, urethane narcosis, intraperitoneal administration.
ED 20% [mg/kg] = the dose at which the blood pressure falls by 20%.
R.E. = relative effectiveness; dihydralazine = 1.00.
[2]Human thrombocytes, in vitro.
EC 50% [mg/l] = the concentration which inhibits the collagen-induced aggregation by 50%.
R.E. = relative effectiveness; acetylsalicyclic acid = 1.00

TABLE 2

| Substance | Inhibition of thrombocyte aggregation[1] | | Anti-hypertensive effect[2] | | Toxicity[3] |
|---|---|---|---|---|---|
| | ED 33% | R.E. | ED 20% | R.E. | LD 50 |
| Example 5 | 0.82 | 163 | 1.16 | 5.9 | 231 |
| Acetylsalicyclic acid | 134 | 1.0 | — | — | 167 |
| Dihydralazine | — | — | 6.85 | 1.0 | 106 |

[1]Rats. Oral administration. In accordance with the maximum effectiveness, Example 5 was administered 2 hours before, and acetylsalicylic acid 4 hours before measuring the aggregation.
ED 33% [mg/kg] = the dose which inhibits the collagen-induced aggregation by 33%.
R.E. = relative effectiveness.
[2]Spontaneously hypertonic rats. Oral administration.
ED 20% [mg/kg] = the dose which lowers the blood pressure by 20% compared to the control group.
[3]Mice. Intraperitoneal administration.

The results (Table 1) show that the compounds according to the invention exert an exceptionally strong inhibiting effect on the collagen-induced aggregation of human thrombocytes. The effect is 291-15,900 times as strong as the effect of the conventional aggregation-inhibiting drug acetylsalicyclic acid.

In addition to the inhibition of thrombocyte aggregation, an anti-hypertensive effect of varying intensity is found. The compounds of Examples No. 5 and No. 7 are respectively 43 and 7.6 times more powerful as anti-hypertensive agents than the conventional antihypertensive agent dihydralazine. A number of other compounds (Examples 1,3,4,8,12 and 16) are about as active as dihydralazine. The anti-hypertensive effect is slight in the case of compounds 9 and 17, but especially in the case of Example 6. In this case, there is a highly specific thrombocyte aggregation-inhibiting effect. From a pharmaco-therapeutic point of view, compounds which inhibit thrombocyte aggregation and lower the blood pressure are as desirable as those which inhibit thrombocyte aggregation but have only little effect on the blood pressure.

We have shown, in the case of the compound of Example 5 (Table 2) that the very strong inhibition of thrombocyte aggregation is also found after oral administration. Furthermore, at the low oral dose of 1.2 mg/kg the substance lowers the blood pressure of spontaneously hypertensive rats by about 20%. The acute toxicity of the compound of Example 5 is somewhat less than that of acetylsalicyclic acid and dihydralazine.

Accordingly, the present invention also relates to therapeutic agents or formulations which in addition to conventional carriers and excipients contain the above compounds as active ingredients, and to the use of such compounds for therapeutic purposes.

It should be noted that 6-(p-chloroacetylaminophenyl)-4,5-dihydropyridaz-3-one and 6-[p-(2-chloropropionylamino)-phenyl]-4,5-dihydropyridaz-3-one are described as intermediates in German Laid-Open Application DOS No. 2,123,246. Anti-inflammatory and antihypertensive properties of acylaminophenyl-dihydropyridazones in which acyl is not substituted by halogen have been described (cf. German Laid-Open Applications DOS Nos. 1,670,158 and DOS 2,150,436). The inhibition of thrombocyte aggregation by the compounds to be used according to the invention is a completely unexpected effect.

The therapeutic agents or formulations are prepared in the conventional manner by compounding a suitable dose with the conventional carriers or excipients and the conventionally used pharmaceutical auxiliaries, in accordance with the desired route of administration. In man, suitable doses are from 1 to 100 mg, oral administration being preferred.

Examples of forms suitable for oral administration are tablets, film tablets, dragees, capsules, pills, powders, solutions, suspensions or forms which exert a depot effect.

For practical use, the compounds to be employed according to the invention are compounded with the excipients conventionally used in Galenic pharmacy. For example, appropriate tablets can be obtained by mixing the active ingredient with conventional auxiliaries, for example inert excipients, eg. dextrose, sugar, sorbitol, polyvinylpyrrolidone, mannitol, calcium carbonate, calcium phosphate or lactose, disintegrating agents, eg. corn starch, alginic acid or polyvinylpyrrolidone, binders, eg. starch or gelatin, lubricants, eg. magnesium stearate or talc, and/or agents added in order to achieve a depot effect, eg. carboxypolymethylene, carboxymethylcellulose, cellulose acetate-phthalate or polyvinyl acetate. The tablets can also consist of several layers.

Similarly, dragees may be prepared by coating cores, produced by methods similar to that described for tablets, with agents conventionally used in dragee coatings, eg. collidone or shellac, gum arabic, talc, titanium dioxide or sugar. The degree coating can also consist of several layers, and the auxiliaries mentioned above, in connection with tablets, may be used in these.

The Examples which follow illustrate the preparation of the novel 6-(p-acylaminophenyl)-4,5-dihydropyridaz-3-ones.

EXAMPLE 1

30.2 g (0.16 mole) of 6-(p-aminophenyl)-4,5-dihydropyridaz-3-one, 18.1 g (0.16 mole) of chloroacetyl chloride and 150 ml of absolute benzene are refluxed for 2 hours. The product is filtered off at room temperature, washed first with benzene and then with water, and dried under reduced pressure at 80° C. 34.6 g (81% of theory) of 6-(p-chloroacetylaminophenyl)-4,5-dihydropyridaz-3-one are obtained as a beige solid which, after recrystallization from dimethylformamide/water, melts, with decomposition, at 233° C.

Analysis for $C_{12}H_{12}ClN_3O_2$: Calculated: C, 54.2; H, 4.5; Cl, 13.3; N, 15.8; O, 12.0%. Found: C, 54.1; H, 4.5; Cl, 13.6; N, 15.8; O, 12.4%.

EXAMPLE 2

(a) 20 g (103 millimoles) of β-(p-aminobenzoyl)-propionic acid and 12.9 g (114 millimoles) of chloroacetyl chloride, together with 200 ml of absolute toluene, are kept for 4 hours at 80° C. The product is filtered off at 10° C., washed with water and dried under reduced pressure at 50° C. 25.1 g (90% of theory) of β-(p-chloroacetylaminobenzoyl)-propionic acid are isolated as light brown crystals which, after recrystallization from acetone, melt at 184°–185° C.

Analysis for $C_{12}H_{12}ClNO_4$: Calculated: C, 53.4; H, 4.5; Cl, 13.1; N, 5.2%. Found: C, 53.6; H, 4.6; Cl, 13.0; N, 5.2%.

(b) 4.0 g (14.8 millimoles) of β-(p-chloroacetylaminobenzoyl)-propionic acid are refluxed with 0.74 g (14.8 millimoles) of hydrazine hydrate and 70 ml of ethanol for 3 hours. After filtering off the product at 10° C. and drying it under reduced pressure at 50° C., 3.3 g (84% of theory) of 6-(p-chloroacetylaminophenyl)-4,5-dihydropyridaz-3-one are obtained as pale yellow crystals (identical with the compound from Example 1, according to its melting point and infrared and NMR spectra).

EXAMPLE 3

6.4 g (31.5 millimoles) of 6-(p-aminophenyl)-5-methyl-4,5-dihydropyridaz-3-one and 4.2 g (37.1 millimoles) of chloroacetyl chloride in 150 ml of absolute benzene are refluxed for 4 hours. The product is filtered off at 0° C., washed with water and recrystallized from ethanol/water. 3.8 g (43% of theory) of 6-(p-chloroacetylaminophenyl)-5-methyl-4,-dihydropyridaz-3-one are obtained as pale yellow crystals melting at 235.5°–236.5° C.

Analysis for $C_{13}H_{14}ClN_3O_2$: Calculated: C, 55.8; H, 5.0; Cl, 12.7; N, 15.0; O, 11.4%. Found: C, 55.8; H, 5.1; Cl, 12.4; N, 15.2; O, 11.9%.

EXAMPLE 4

47.2 g (0.25 mole) of 6-(p-aminophenyl)-4,5-dihydropyridaz-3-one and 35.6 g (0.28 mole) of 2-chloropropionyl chloride in 250 ml of absolute benzene are refluxed for 2 hours. The product is filtered off at 10° C., washed first with benzene and then with water and dried under reduced pressure at 100° C. 64.8 g (93% of theory) of 6-[p-(2-chloropropionylamino)-phenyl]-4,5-dihydropyridaz-3-one are obtained as a beige solid which, after recrystallization from propanol, melts, with decomposition, at 243°–244° C.

Analysis for $C_{13}H_{14}ClN_3O_2$: Calculated: C, 55.8; H, 5.0; Cl, 12.7; N, 15.0; O, 11.4%. Found: C, 55.2; H, 4.9; Cl 13.1; N, 14.9; O, 11.9%.

EXAMPLE 5

6.0 g (29.6 millimoles) of 6-(p-aminophenyl)-5-methyl-4,5-dihydropyridaz-3-one and 4.1 g (32.3 millimoles) of 2-chloropropionyl chloride in 100 ml of absolute toluene are kept at 80° C. for 4 hours. The product is filtered off at 10° C., washed with water and dried under reduced pressure at 50° C. 7.9 g (91% of theory) of 6-[p-(2-chloropropionylamino)-phenyl]-5-methyl-4,5-dihydropyridaz-3-one are isolated as beige crystals which, after recrystallization from methanol, melt at 215°–217° C.

Analysis for $C_{14}H_{16}ClN_3O_2$: Calculated: C, 57.2; H, 5.5; Cl, 12.1; N, 14.3; O, 10.9%. Found: C, 57.1; H, 5.5; Cl, 12.1; N, 14.6; O, 11.2%.

EXAMPLE 6

18.9 g (0.10 mole) of 6-(p-aminophenyl)-4,5-dihydropyridaz-3-one and 15.2 g (0.12 mole) of 3-chloropropionyl chloride in 90 ml of absolute benzene are refluxed for 2 hours. The product is filtered off at 10° C., washed first with benzene and then with water, and dried under reduced pressure at 100° C. 27.2 g (97% of theory) of 6-[p-(3-chloropropionylamino)-phenyl]-4,5-dihydropyridaz-3-one are obtained as a colorless substance which, after recrystallization from dimethylformamide/water, melts, with decomposition, at 226°–227° C.

Analysis for $C_{13}H_{14}ClN_3O_2$: Calculated: C, 55.8; H, 5.0; Cl, 12.7; N, 15.0; O, 11.4%. Found: C, 56.0; H, 5.3; Cl, 12.7; N, 15.0; O, 11.4%.

EXAMPLE 7

6.0 g (29.6 millimoles) of 6-(p-aminophenyl)-5-methyl-4,5-dihydropyridaz-3-one and 4.1 g (32.3 millimoles) of 3-chloropropionyl chloride are stirred with 100 ml of absolute toluene for 4 hours at 80° C. The product is filtered off at 10° C., washed with water and dried under reduced pressure at 50° C. 5.8 g (67% of theory) of 6-[p-(3-chloropropionylamino)-phenyl]-5-methyl-4,5-dihydropyridaz-3-one are obtained as beige crystals which, after recrystallization from methanol, melt, with decomposition, at 221°–223° C.

Analysis for $C_{14}H_{16}ClN_3O_2$: Calculated: C, 57.2; H, 5.5; Cl, 12.1; N, 14.3; O, 10.9%. Found: C, 57.2; H, 5.6; Cl, 12.0; N, 14.4; O, 11.6%.

EXAMPLE 8

6.0 g (29.6 millimoles) of 6-(p-aminophenyl)-5-methyl-4,5-dihydropyridaz-3-one and 4.6 g (32.6 millimoles) of 4-chlorobutyryl chloride in 100 ml of absolute toluene are kept for 6 hours at 80° C. The product is filtered off at 10° C., washed with water and dried under reduced pressure at 50° C. 8.5 g (93% of theory) of 6-[p-(4-chlorobutyrylamino)-phenyl]-5-methyl-4,5-dihydropyridaz-3-one are obtained as beige crystals which, after recrystallization from methanol, melt at 176°–178° C.

Analysis for $C_{15}H_{18}ClN_3O_2$: Calculated: C, 58.6; H, 5.9; Cl, 11.5; N, 13.7; O, 10.4%. Found: C, 58.4; H, 5.9; Cl, 11.4; N, 13.8; O, 10.9%.

The Table which follows lists further Examples. These dihydropyridazones were prepared by the method described in Example 7.

and the mixture is pressed to give tablets weighing 240 mg each.

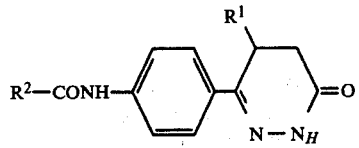

| Example | R¹ | R² | Melting point [°C.] | Analysis (%) calc/found | C | H | Hal | N |
|---|---|---|---|---|---|---|---|---|
| 9 | —CH₃ | CH₃—CH₂—CH(Br)— | 213–214 (decomposition) (DMF/water) | calc: found: | 51.2 51.3 | 5.1 5.1 | 22.7 22.3 | 11.9 12.2 |
| 10 | —H | CH₃—CH₂—CH(Br)— | 201–202 (DMF/water) | calc: found: | 49.7 49.4 | 4.8 4.8 | 23.6 23.0 | 12.4 12.1 |
| 11 | —CH₃ | Cl—CH₂—C(CH₃)₂— | 203–204 (DMF/water) | calc: found: | 59.7 59.6 | 6.3 6.3 | 11.0 10.8 | 13.1 13.3 |
| 12 | —CH₃ | Br—CH₂—C(CH₃)₂— | 189–190 (DMF/water) | calc: found: | 52.5 52.6 | 5.5 5.8 | 21.8 21.2 | 11.5 11.9 |
| 13 | —H | Cl—CH₂—C(CH₃)₂— | 200–202 (DMF/water) | calc: found: | 58.5 58.6 | 5.9 6.0 | 11.5 11.3 | 13.7 13.7 |
| 14 | —H | Br—CH₂—C(CH₃)₂— | 213–214 (Propanol/water) | calc: found: | 51.2 51.5 | 5.1 5.2 | 22.7 21.9 | 11.9 12.1 |
| 15 | —H | Cl—CH₂—CH₂—CH₂— | 190–191 (DMF/water) | calc: found: | 57.2 57.4 | 5.5 5.6 | 12.1 11.7 | 14.3 14.4 |
| 16 | —CH₃ | CH₃—CH(Br)— | 223–224 (decomposition) (DMF/water) | calc: found: | 49.7 50.1 | 4.8 4.9 | 23.6 23.4 | 12.4 12.4 |
| 17 | —CH₃ | CH₃—C(CH₃)(Br)— | 205–206 (decomposition) (Propanol/water) | calc: found: | 51.2 51.1 | 5.1 5.4 | 22.7 21.9 | 11.9 12.2 |

Examples of formulations, prepared in the conventional manner, are given below:

1. Tablets:

| | |
|---|---|
| Active ingredient | 10 mg |
| Polyvinylpyrrolidone (mean molecular weight 25,000) | 170 mg |
| Polyethylene glycol (mean molecular weight 4,000) | 14 mg |
| Hydroxypropylmethylcellulose | 40 mg |
| Talc | 4 mg |
| Magnesium stearate | 2 mg |
| | 240 mg |

The active ingredient is moistened with a 10% strength aqueous solution of polyvinylpyrrolidone and forced through a sieve of mesh width 1.0 mm. The granules are dried at 50° C. and mixed with polyethylene glycol (mean molecular weight 4,000), hydroxypropylmethylcellulose, talc and magnesium stearate, 2. Dragees

| | |
|---|---|
| Active ingredient | 10 mg |
| Lactose | 90 mg |
| Corn starch | 60 mg |
| Polyvinylpyrrolidone | 6 mg |
| Magnesium stearate | 1 mg |
| | 167 mg |

The mixture of the active ingredient with lactose and corn starch is converted to granules by moistening with an 8% strength aqueous solution of the polyvinylpyrrolidone and forcing through a 1.5 mm sieve. The granules are dried at 50° C. and forced through a 1.0 mm sieve. The granules thus obtained are mixed with magnesium stearate and molded to give dragee cores. The latter are coated in the conventional manner with a shell which essentially consists of sugar and talc.

We claim:

1. A 6-(p-acylaminophenyl)-4,5-dihydropyridaz-3-one of the formula I

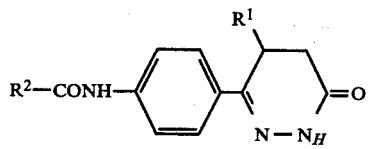

where $R^1$ is alkyl of 1 to 3 carbon atoms and $R^2$ is halogen-substituted alkyl of 1 to 6 carbon atoms.

2. A compound of the formula I, where $R^1$ is methyl and $R^2$ is halogen-substituted alkyl of 1 to 4 carbon atoms.

3. 6-[p-(2-Chloropropionylamino)-phenyl]-5-methyl-4,5-dihydropyridaz-3-one.

4. A therapeutic composition for inhibiting thrombocyte aggregation which comprises a therapeutically effective amount of a compound of the formula I

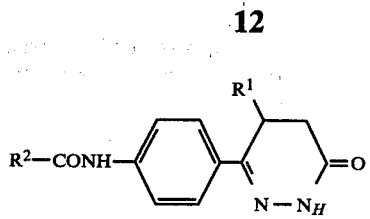

where $R^1$ is alkyl of 1 to 3 carbon atoms and $R^2$, is halogen-substituted alkyl of 1 to 6 carbon atoms, together with conventional carriers and excipients.

5. The therapeutic composition of claim 4 which contains 6-[p-(2-chloropropionylamino)-phenyl]-5-methyl-4,5-dihydropyridaz-3-one as the active ingredient.

6. A method of treating thrombotic diseases which comprises: administering in dosage form to the subject to be treated the composition of claim 4, the amount of active compound of the formula I in each dose being from 1 to 100 mg.

* * * * *